United States Patent [19]

Montiel

[11] 4,135,527

[45] Jan. 23, 1979

[54] EYELASH EXTENDER PRODUCT AND METHOD OF APPLICATION

[76] Inventor: Alexandra Montiel, 50 Jefferson St., Brooklyn, N.Y. 11206

[21] Appl. No.: 761,339

[22] Filed: Jan. 21, 1977

[51] Int. Cl.² ............................................. A45D 40/26
[52] U.S. Cl. .................................................. 132/88.7
[58] Field of Search ...................... 132/88.7, 88.5, 53; 401/122, 128; 15/257.05; 424/63, 359

[56] References Cited

U.S. PATENT DOCUMENTS

| | | | |
|---|---|---|---|
| 3,033,213 | 5/1962 | Joss | 401/128 |
| 3,084,374 | 4/1963 | Ziegler | 401/122 |
| 3,280,421 | 10/1966 | Davidson | 401/122 |
| 3,605,764 | 9/1971 | Ehrlich | 132/88.7 |
| 3,863,654 | 2/1975 | Morane | 132/88.7 |
| 3,885,578 | 5/1975 | Hicks | 132/88.5 |

OTHER PUBLICATIONS

M. S. Balsam & E. Sagarin, Cosmetics Science and Technology, Second Edition, 1972, pp. 412-413.
Cosmetics Science and Technology, 1957, pp. 291 and 294, Editor Edward Sagarin.

Primary Examiner—G.E. McNeill

[57] ABSTRACT

An improved product for extending the length of and enhancing the appearance of eyelashes and the method of applying it is disclosed. Separate containers of a liquid mascara adhesive and synthetic fiber filaments are each provided with a suitable applicator and means for regulating the amount of material removed from each container by its applicator each time it is used. The method of application in brief involves moistening the eyelashes with liquid adhesive, applying the fiber filaments, and coating the resultant extended lashes with more liquid mascara adhesive.

11 Claims, 7 Drawing Figures

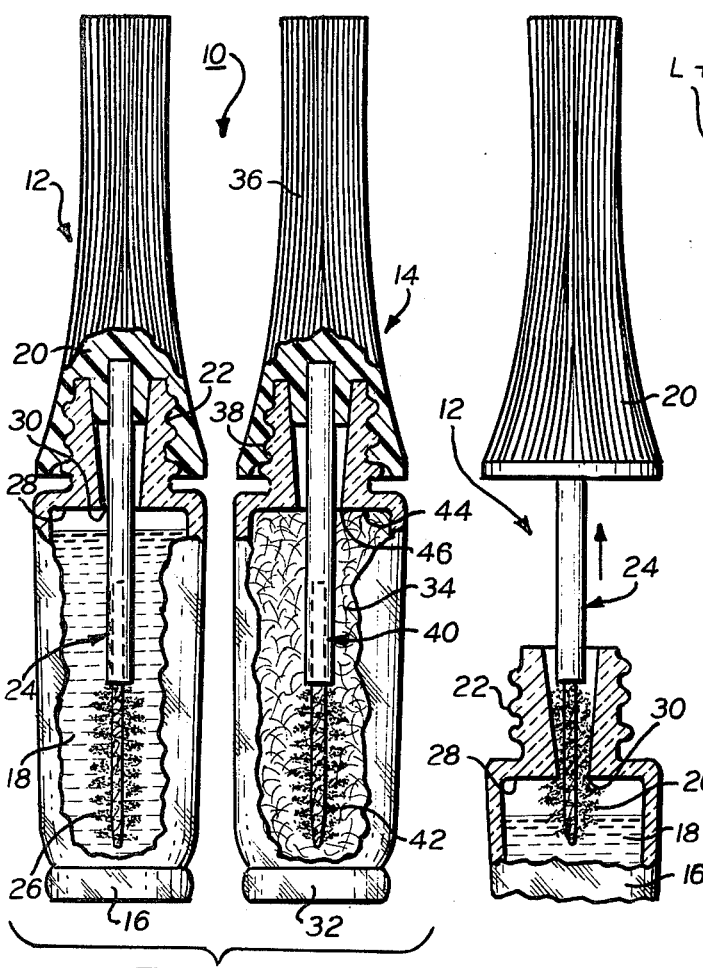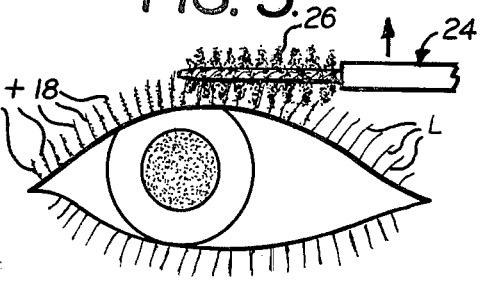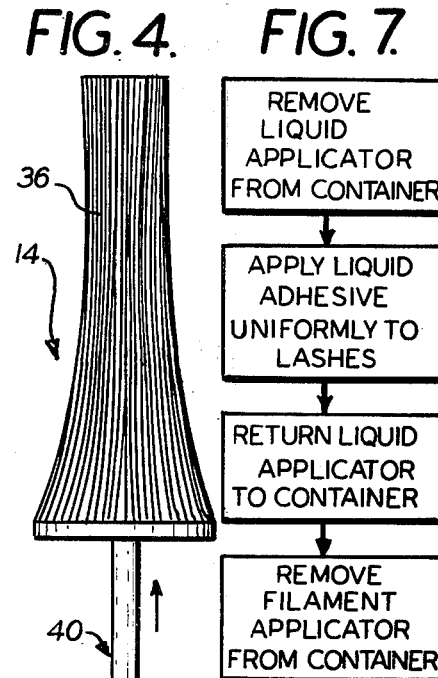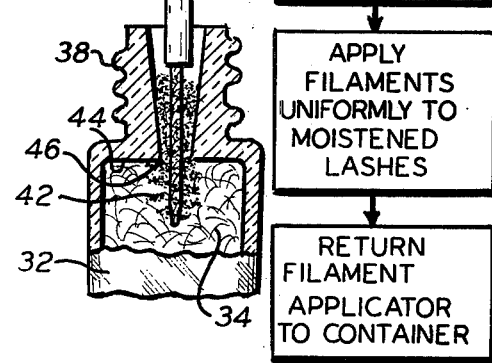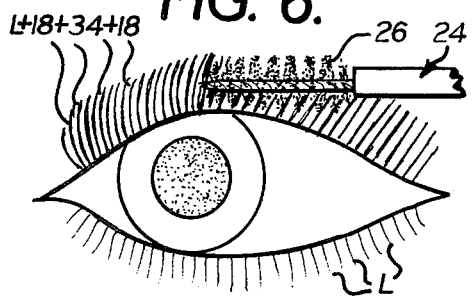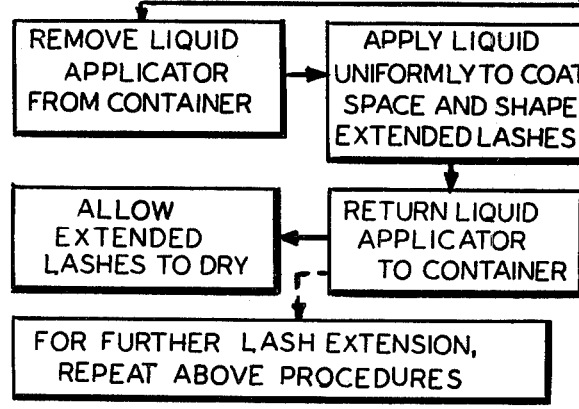

EYELASH EXTENDER PRODUCT AND METHOD OF APPLICATION

BACKGROUND OF THE INVENTION

The desire to improve the appearance of eyelashes by lengthening, thickening and coloring them, or by substituting false lashes for them, is not satisfactorily met by products of the prior art now available. Those preparations which rely solely on coating the existing eyelashes do thicken them but cannot increase their apparent length significantly; while those products which contain fiber filaments admixed cannot be applied to give an evenly distributed groomed appearance, but instead leave the lashes looking uneven, matted and gummy. A preparation employing the "one-on-one technique", wherein filaments are glued into place one at a time, presents the problem of frustratingly laborious, painstaking, time-consuming work to use it. And false eyelashes, previously mounted on a strip and designed to be glued to the eyelid, are uncomfortable to wear and can be kept in place for only a few hours at a time.

It is therefore apparent that the art to date has not met the need for an eyelash extender and enhancer which can be simply, quickly and safely applied and can give a smooth, luxuriant, long-lasting appearance.

SUMMARY OF THE INVENTION

It is the principal object of this invention to overcome the deficiencies of the prior art mentioned above. The product disclosed herein does indeed provide the qualities of easy, rapid, trouble-free application and outstanding appearance results.

Specifically, the inventive concept embodied herein includes the provision of a two-component system, each component having its own container and its own applicator. Each container is provided with a restricted opening, the diameter of which is smaller than the outer diameter of its associated applicator; removal of either applicator from its container results in the applicator being compressed sufficiently to force excess material back into the container, thus dispensing an appropriate quantity and avoiding dripping, spilling or scattering of excess material during its application.

The two components which comprise the product of this invention are: a liquid mascara adhesive and a quantity of synthetic fiber filaments. The adhesive is formulated to perform three functions: it has a hydrolyzed protein as its binder, serving to condition and strengthen the natural eyelashes; it contains mascara ingredients to color both the natural lashes and the synthetic filaments; and it acts adhesively to bind together, to coat and to hold in shape the lashes and filaments, which together form extended uniform thick luxuriant-looking eyelashes. The best mode for practising this invention now contemplated utilizes a water-dispersed liquid adhesive with no volatile organic solvents which might be irritating to the eye when applied to the lashes. A typical hypo-allergenic liquid mascara adhesive suitable for use in this product may include, by way of example, the following list of ingredients: water, beeswax, shellac, glyceryl stearate, morpholine, PVP, oleic acid, imidazolidinyl urea, quaternium-15, methyl paraben, propyl paraben, trisodium EDTA, hydrolyzed animal protein and carbon black. Mascara colors other than black may be supplied by substituting for the carbon black such coloring matter as iron oxides, ultramarine blue, or chromium oxide greens.

The synthetic fiber filaments of this invention must be of a length approximating 2-4 millimeters, a cross-sectional diameter preferably considerably less than that of a human hair or lash; in addition, they must be as light in weight as possible. It has been experimentally established that human hair and natural fibers are too coarse and heavy to be used in practising this invention; that fiber filaments shorter than 2 millimeters do not handle well nor hold in place satisfactorily. While synthetic fiber filaments made from other compounds and meeting the physical requirements of size, length and density may be incorporated into the lash-extending product, the most desirable fiber filament material known at this time for this purpose is rayon. Rayon filaments not only cooperate and combine very well with the liquid adhesive, but have a significant added advantage: if a rayon filament should accidentally drop from its applicator or from a lash into an eye, it will tend to dissolve in the eye fluid without irritating or damaging the eye. Specifically, the preferred filament material is rayon flock, identified commercially as #422204, which may be packaged either in its original white color to be used with light-color mascara, or pre-colored for darker lashes.

The product of this invention is applied by first moistening the natural eyelashes with liquid mascara adhesive, using the liquid applicator withdrawn from its container to convey an adequate portion of adhesive to the lashes and to distribute an even liquid coating thereon. After returning the liquid applicator to its container, the fiber filament applicator is pulled out through the restricted opening of its container; this action not only leaves excess filaments behind in the container, but also serves to force those fibers that are withdrawn into sufficiently firm engagement with the bristles of the brush applicator so that any dropping or scattering of loose filaments is minimized. Now the filaments are applied to the moistened lashes, wiping them with the applicator outwardly from the eyelid-attached ends of the lashes in smooth even strokes. The filament applicator is restored to its container, and the adhesive applicator is again taken in hand to coat the extended lashes with a color-evening protective finish; during this procedure, the extended lashes, by appropriate applicator strokes, may be spaced, shaped or curled at will. Return of the liquid applicator to its container and allowance of a few minutes for drying completes the extended lash application. If, however, even further extension of the lashes is desired, the final drying may be omitted, and a second application of filaments may be used, followed by coating with liquid and permitting to dry as above.

It may be noted that while the extended lashes provided by this invention may be removed readily, if desired, by washing with soap and water, an application can survive successfully for two weeks or longer if excessive wetting is avoided. When account is taken of the fact that normal regenerative cycle of the human lash is approximately 20 days, the old lashes falling away and replaced by fresh ones, it is evident that the product herein described offers a durability closely approaching a maximum practical limit. It may be noted also that, if desired, the liquid mascara adhesive of this invention may be used alone for coloring, conditioning, thickening and enhancing the appearance of natural lashes.

Finally, it should be emphasized that the extended lashes created by the proper application of this product, easily accomplished as outlined above, are vastly superior in quality and appearance to those of the prior art, with each lash extending clearly independent of its neighbors in smoothly groomed full bodied luxuriant display.

The details of a preferred embodiment of this invention will be described clearly and fully in connection with the accompanying drawings, wherein:

DRAWINGS

FIG. 1 illustrates the components of the eyelash-extending product of this invention in a front elevational view, partly broken away;

FIG. 2 is a partial elevational view, partly broken away, showing the liquid mascara adhesive applicator being removed from its container;

FIG. 3 shows the liquid mascara adhesive applicator in use, moistening a row of eyelashes;

FIG. 4 is a partial elevational view, partly in section, showing the fiber filament applicator being withdrawn from its container;

FIG. 5 illustrates the fiber filament applicator in use, adhesively applying extending filaments to a row of moistened eyelashes;

FIG. 6 shows the liquid adhesive applicator in use again, coating, spacing and shaping an extended row of lashes; and FIG. 7 diagrammatically outlines the method of application to be used in the practice of this invention.

DESCRIPTION OF A PREFERRED EMBODIMENT

As shown in FIG. 1 the product, generally designated 10, comprises companion units 12 and 14. Liquid mascara adhesive unit 12 has container 16, here shown as a glass bottle, filled with water-dispersed, hydrolyzed-protein-based liquid mascara adhesive 18. Screw cap 20, threadedly engaging threads 22 of bottle 16, fixedly carries liquid mascara adhesive applicator 24, with its wire-supported bristle brush free-end portion 26 centrally disposed within the lower section of bottle 16. At its upper shoulder 28, bottle 16 is provided with restricted opening 30, which has a diameter smaller than the outer diameter of bristle brush portion 26 of applicator 24. As best seen in FIG. 2, when screwcap 20 is unscrewed from threads 22 of bottle 16 and applicator 24 is being withdrawn, brush portion 26 is squeezed by the walls of restricted opening 30, forcing any excess liquid back into bottle 16. FIG. 3 shows lashes L being coated with liquid adhesive 18, with applicator brush 26 being stroked outwardly.

Similarly, fiber filament unit 14 is shown as comprising a glass bottle container 32 for holding rayon flock filaments 34. Screwcap 36 engages bottle threads 38 and fixedly carries filament applicator 40, with its wire-held bristle brush free-end portion 42 centrally disposed within lower portion of bottle 32. At upper shoulder 44 of bottle 32, restricted opening 46 causes excess fiber filaments 34 to be left behind when brush 42 of applicator 40 is withdrawn from the bottle, as shown in FIG. 4. At the same time, those filaments 34 which remain on brush 42 are pressed onto the bristles so that dropping or scattering of loose filaments, while applicator 40 is being conveyed to lashes L, is minimized. FIG. 5 shows filaments 34 being applied to moistened lashes L by outward stroking of brush 42.

In FIG. 6, brush 26 of liquid adhesive applicator 24 is shown applying a finish coating of liquid adhesive 18 to extended lashes L, at the same time spacing and shaping them. FIG. 7 describes in diagrammatic form the procedural steps involved in the method of application of the product of this invention.

It should be apparent that modifications or variations in the various elements shown in the drawings and described above may be made without departing from the essence or spirit of this invention. Thus, for example, the containers shown may be altered in size, shape, and material; other types of container closures may be used; different applicators, differently mounted, are possible, especially for the liquid adhesive component, for which the bristle brush could be replaced by sponge or a pile fabric.

I claim:

1. A product for extending the length of and enhancing the appearance of natural eyelashes, which comprises:
    a liquid mascara adhesive;
    first container means for holding said liquid mascara adhesive;
    first applicator means for applying said liquid mascara adhesive to the natural eyelashes;
    loose synthetic fiber filaments;
    second container means for holding said loose synthetic fiber filaments;
    second applicator means for applying said synthetic fiber filaments to the natural eyelashes moistened by first applying said liquid mascara adhesive to the eyelashes by said first applicator means;
    said fiber filaments, when applied by outwardly directed strokes of said second applicator means along the length of the moistened natural eyelashes, being held on the natural eyelashes by said liquid mascara adhesive and being oriented in parallel and overlying relationship with the natural eyelashes, so that each resultant composite lash thus created is of uniform apearance throughout its length, is independently spaced from its adjacent composite lashes and extends outwardly to a length substantially greater than the length of the natural eyelash.

2. An eyelash-extending product as in claim 1, wherein said liquid mascara adhesive has a hydrolyzed protein binder and is water dispersed.

3. An eyelash-extending product as in claim 1, wherein said synthetic fiber filaments have a length of 2 to 4 millimeters.

4. An eyelash-extending product as in claim 1, wherein said synthetic fiber filaments are rayon flock.

5. An eyelash-extending product as in claim 1, where said container means for holding said liquid mascara adhesive and said container means for holding said synthetic fiber filaments are each provided with means for regulating the amount of material removed from each of said container means by each of said applicator means.

6. An eyelash-extending product as in claim 5, wherein said means for regulating the amount of material removed comprises each of said container means having an opening the inside diameter of which is smaller than the maximum outside diameter of each of said applicator means.

7. An eyelash-extending product as in claim 1, wherein said applicator means for applying said synthetic fiber filaments comprises a bristle brush.

8. An eyelash-extending product as in claim 1, the method of application for which comprises the steps of:

removing liquid applicator from its container;
applying liquid adhesive uniformly to eyelashes;
returning liquid applicator to its container;
removing filament applicator from its container;
applying filaments uniformly to moistened eyelashes with outwardly directed strokes of filament applicator;
returning filament applicator to its container;
removing liquid applicator from its container;
applying liquid adhesive uniformly to coat, space and shape substantially extended composite lashes;
returning liquid applicator to container; and
allowing substantially extended composite lashes to dry.

9. A method of extending the length of and enhancing the appearance of natural eyelashes, which comprises the sequential steps of:

applying liquid mascara adhesive uniformly to the eyelashes by a first applicator;
applying loose synthetic fiber filaments uniformly to the moistened eyelashes by outwardly directed strokes of a second applicator; and
applying liquid mascara adhesive uniformly to the combined natural eyelashes and said filaments adhered in parallel overlying relationship thereto by said first applicator to coat, space and shape the resultant substantially extended composite lashes.

10. An eyelash-extending product according to claim 1, wherein each said resultant composite lash extends to a length in the range from one and one-half to two and one-half times the length of the natural eyelash.

11. The method according to claim 9, wherein said resultant composite lashes extend to a length in the range from one and one-half to two and one-half times the length of the natural eyelashes.

* * * * *